United States Patent
Kazami et al.

(10) Patent No.: US 7,183,412 B2
(45) Date of Patent: Feb. 27, 2007

(54) ESTER OR AMIDE DERIVATIVES

(75) Inventors: Jun-ichi Kazami, Tsukuba (JP); Masato Watanabe, Tokyo (JP); Takuya Hirata, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 105 days.

(21) Appl. No.: 10/992,134

(22) Filed: Nov. 19, 2004

(65) Prior Publication Data

US 2005/0090497 A1    Apr. 28, 2005

Related U.S. Application Data

(62) Division of application No. 10/363,033, filed as application No. PCT/JP01/07307 on Aug. 27, 2001, now Pat. No. 6,822,098.

(30) Foreign Application Priority Data

Aug. 29, 2000  (JP)  .............................. 2000-258498

(51) Int. Cl.
  *C07D 215/38* (2006.01)
  *C07D 215/44* (2006.01)
(52) U.S. Cl. ...................................... 546/156; 546/157
(58) Field of Classification Search ................ 546/156, 546/157; 514/312
See application file for complete search history.

(56) References Cited

FOREIGN PATENT DOCUMENTS

| EP | 0 498 721 | * 8/1992 |
|----|-----------|----------|
| EP | 811613 | 12/1997 |
| JP | 55151511 | 11/1980 |
| JP | 09309879 | 12/1997 |
| JP | 10-279561 | 10/1998 |
| WO | WO 96/13485 | 5/1996 |
| WO | 96/33190 | * 10/1996 |
| WO | WO 96/36608 | 11/1996 |
| WO | WO 97/12868 | 4/1997 |

OTHER PUBLICATIONS

Bradbury, R.H. et al., J. Med. Chem., (1992) vol. 35, pp. 4027-4038.
Wright, R. et al., abstract of CA 103:104824, Synthesis, (1984) vol. 12, pp. 1058-1061.
Coltman S.C. W. et al., Abstract CA 101L:7005, Synthesis, (1984), vol. 2, pp. 150-152.

* cited by examiner

*Primary Examiner*—D. Margaret Seaman
(74) *Attorney, Agent, or Firm*—Finnegan, Henderson, Farabow, Garrett & Dunner LLP

(57) ABSTRACT

An ester or amide derivative represented by the general formula (I) or a pharmaceutically acceptable salt thereof. Particularly, an ester or amide derivative of 4-oxo-1,4-dihydroqunoline-2-carboxylic acid represented by the general formula (I') or (I"), or a pharmaceutically acceptable salt thereof.

27 Claims, No Drawings

ESTER OR AMIDE DERIVATIVES

RELATED APPLICATIONS

This application is a divisional of application Ser. No. 10/363,033, filed Feb. 28, 2003, now U.S. Pat. 6,822,098; which is a national stage application under 35 U.S.C. § 371 of international application PCT/JP01/07307, filed Aug. 27, 2001, each of which are incorporated by reference.

TECHNICAL FIELD

The present invention relates to a novel ester or amide derivative, particularly an ester or amide derivative of 4-oxo-1,4-dihydroqunoline-2-carboxylic acid, or a pharmaceutically acceptable salt thereof, and a drug composition containing it as an active ingredient, particularly a preventive or remedy for *Helicobacter pylori* infectious diseases.

BACKGROUND ART

*Helicobacter pylori* is a pathogenic bacterium discovered in 1983 and is called a background pathogenic factor of peptic ulcers (such as gastric ulcer and duodenal ulcer), inflammations (such as gastritis), diseases of upper digestive tracts such as gastric cancer, MALT (mucosa-associated lymphoid tissue) lymphoma, or chronic heart disease. At present, studies on the therapy of *Helicobacter pylori* infectious diseases are being actively made. As the therapy, there are many reports for the purposes of bacterial elimination and prevention of recurrence, as described below. For example, there is numerated administration of a single drug of, e.g., bismuth, antibiotic, proton pump inhibitor (PPI), or anti-ulcer agent, or polypharmacy (such as two-drug therapy and three-drug therapy) comprising a combination of the foregoing drugs (see *Internal Medicine, Special Issue*, Vol. 78 (1), 1996, by Nankodo). However, these therapies still involve many problems to be solved, such as high frequency of administration of the drug(s), necessity of administration of a lager amount of the drug(s) than the regular dose, crisis of diarrhea or constipation by administration of the drug(s), and generation of resistant bacteria.

As an anti-*helicobacter pylori* agent, EP811613 discloses derivatives of 4-oxo-1,4-dihydroquinoline or naphthyridine in terms of the following general formula. In the general formula, the substituent ($R_2$ group) at the 2-position of the ring is a $C_1$ to $C_{10}$ alkyl group, a ($C_1$ to $C_{10}$ alkyl)phenyl group, a $C_2$ to $C_{10}$ alkenyl group, a ($C_2$ to $C_{10}$ alkenyl)phenyl group, a $C_2$ to $C_{10}$ alkynyl group, a ($C_2$ to $C_{10}$ alkynyl)phenyl group, a phenyl group, a naphthyl group, a furyl group, a thiophenyl group, or a pyridyl group.

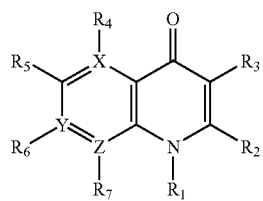

Further, JP-A-10-132784 discloses the following. 3-methyl-4-oxo-1,4-dihydroquinone derivative as an anti-*helicobacter pylori* agent, in which, however, the substituent at the 2-position is a nonenyl group.

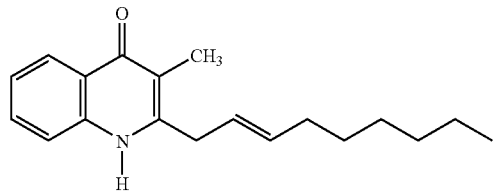

However, creation of a compound having a stronger anti-*helicobacter pylori* action by single and oral administration is being demanded.

On the other hand, as derivatives of a 3-alkyl-4-oxo-1,4-dihydroquinoline-2-carboxylic acid, in DE1913466, *Pol. J. Pharmacol. Pharm.*, 33(5), 539–544, 1981, *Indian. J. Pharm.*, 39(1), 13–15, 1977, *J. Indian Chemical Society*, 50(3), 217–218, 1973, and *J. Indian Chemical Society*, 51(11), 967–969, 1974, there are disclosed compounds having an ethoxycarbonyl group or a (substituted or unsubstituted) $NH_2$—NH—CO— group at the 2-position of the quinoline ring. However, any of these compounds are merely a synthesis intermediate or are merely reported that they have an anti-amoeba activity. These documents neither disclose nor suggest their anti-*helicobacter pylori* activity.

DISCLOSURE OF THE INVENTION

We, the present inventors made extensive and intensive investigations with respect to compounds having an anti-*helicobacter pylori* activity. As a result, it has been found that novel ester or amide derivatives of 4-oxo-1,4-dihydroquinoline-2-carboxylic acid, which are different in terms of structure from the conventional compounds in the point that on the 1,4-dihydroquinoline ring or 1,4-dihydronaphthyridine ring, not only a substituent at the 2-position is an ester residue or a substituted amide group, but also a substituent at the 3-position is an alkyl group, (1) have a strong and selective anti-bacterial action against *Helicobacter pylori*, (2) have a strong anti-bacterial action against *Helicobacter pylori* within digestive tracts by oral administration to mammals, and (3) are useful in the bacterial elimination therapy against patients infected with *Helicobacter pylori*.

Specifically, the invention relates to a novel ester or amide derivative represented by the following general formula (I) or a salt thereof:

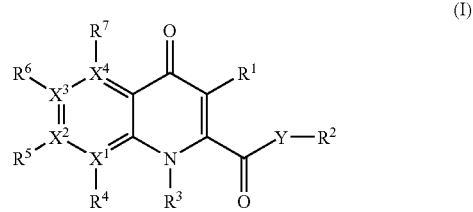

(I)

wherein:
$X^1$ to $X^4$ each independently represents C or N, provided that at least one of $X^1$ to $X^4$ represents C;
Y represents O or NH;
$R^1$ represents a $C_1$ to $C_6$ alkyl group;
$R^2$ represents (a) a $C_1$ to $C_{10}$ alkyl group, provided that when X represents O, $R^2$ represents a $C_3$ to $C_{10}$ alkyl group, or (b) an aryl-$C_1$ to $C_{10}$ alkyl group, a heteroaryl-$C_1$ to $C_{10}$ alkyl group, or a cycloalkyl-$C_1$ to $C_{10}$ alkyl group, provided that any carbon-carbon bond of the $C_1$ to $C_{10}$ alkyl group may be inserted by —O—, —$NR^8$—, or —$S(O)_n$—, wherein $R^8$ represents H or a $C_1$ to $C_6$ alkyl group, and n is 0, 1 or 2, and that the aryl, heteroaryl and cycloalkyl may each be substituted with from one to three of halogen, $C_1$ to $C_6$ alkyl, $C_1$ to $C_6$ alkyl-O—, nitro, cyano, amino, hydroxycarbonyl, $C_1$ to $C_6$ alkyl-NH—, or di-$C_1$ to $C_6$ alkyl=N—;

$R^3$ represents H, a $C_1$ to $C_6$ alkyl group, an aryl-$C_1$ to $C_6$ alkyl group, a heteroaryl-$C_1$ to $C_6$ alkyl group, a cycloalkyl-$C_1$ to $C_6$ alkyl group, an aryl group, a heteroaryl group, or a cycloalkyl group, provided that the aryl, heteroaryl and cycloalkyl may each be substituted with from one to three of halogen, $C_1$ to $C_6$ alkyl, $C_1$ to $C_6$ alkyl-O—, nitro, cyano, amino, hydroxycarbonyl, $C_1$ to $C_6$ alkyl-NH—, or di-$C_1$ to $C_6$ alkyl=N—; and $R^4$ to $R^7$ may be the same or different and each represents H, a halogen, a nitro group, a cyano group, an amino group, a hydroxycarbonyl group, a $C_1$ to $C_6$ alkyl group, a $C_1$ to $C_6$ alkyl-O— group, a $C_1$ to $C_6$ alkyl-NH group, or a di-$C_1$ to $C_6$ alkyl=N— group, provided that in the case where $X^1$ to $X^4$ each represents N, $R^4$ to $R^7$ to be bound thereto are not present and that $R^3$ and $R^4$ may be taken together to form a linear or branched $C_1$ to $C_8$ alkylene which may be inserted by N, O or S.

Also, the invention relates to a drug composition comprising the ester or amide derivative represented by the foregoing general formula (I) or its pharmaceutically acceptable salt and a pharmaceutically acceptable carrier, a particularly a drug composition as a preventive or remedy for *Helicobacter pylori* infectious diseases.

The compound (I) of the invention is structurally characterized in that a substituent at the 2-position of the 1,4-dihydroquinoline ring or 1,4-dihydronaphthyridine ring is an ester residue or an substituted amide group and is superior to the known compounds having a hydrocarbon group as the substituent at the 2-position in the point that it undergoes strong bacterial elimination against *Helicobacter pylori* within digestive tracts by oral administration to mammals.

The compound (I) of the invention will be hereunder described in detail.

Examples of the "halogen" include a fluorine atom, a chlorine atom, a bromine atom, and an iodine atom.

The term "alkyl" means a linear or branched saturated hydrocarbon group. Specific examples of the $C_1$ to $C_{10}$ alkyl include a methyl group, an ethyl group, a propyl group, a butyl group, a pentyl group, a hexyl group, a heptyl group, an octyl group, a nonyl group, a decyl group, and structural isomers thereof (such as an isopropyl group). Specific examples of the $C_1$ to $C_6$ alkyl include a methyl group, an ethyl group, a propyl group, a butyl group, a pentyl group, a hexyl group, and structural isomers thereof (such as an isopropyl group). Specific examples of the $C_6$ to $C_8$ alkyl include a hexyl group, a heptyl group, an octyl group, and structural isomers thereof (such as a methylhexyl group).

The term "alkylene" means a divalent group resulted from removal of hydrogen from the foregoing alkyl. Specific examples of the $C_1$ to $C_8$ alkylene include methylene, ethylene, propylene, butylene, pentylene, hexylene, heptylene, octylene, and structural isomers thereof (such as 2-methylpropylene).

The term "aryl" means an aromatic hydrocarbon group, and preferably a $C_6$ to $C_{14}$ aryl. Specific examples include phenyl, naphthyl, and biphenyl, and particularly preferably phenyl.

The term "heteroaryl" means a 5-membered or 6-membered monocyclic heteroaryl having from 1 to 4 hetero atoms selected from N, S and O, or a bicyclic heteroaryl fused with a benzene ring, which may be partially saturated. Examples of the monocyclic heteroaryl include furyl, thienyl, pyrrolyl, imidazolyl, pyrazolyl, thiazolyl, oxazolyl, pyridyl, pyrazinyl, pyrimidyl, triazolyl, thiazolyl, pyridazinyl, triazinyl, oxazolyl, and pyrimidyl. Examples of the bicyclic heteroaryl include benzofuranyl, benzothienyl, benzothiadiazoyl, benzothiazolyl, benzoimidazolyl, indolyl, quinolyl, isoquinolyl, and quinoxalinyl. Of these are preferable 5-membered or 6-membered monocyclic heteroaryls, with furyl, thienyl, imidazolyl, thiazolyl and pyridyl being more preferable.

The term "cycloalkyl" means a saturated hydrocarbon group having from 3 to 8 carbon atoms. Specific examples include cyclopropyl, cyclobutyl, cyclopentyl, cyclohexyl, cycloheptyl, and cyclooctyl.

In the general formula of the invention, specific examples of the ring represented by the formula:

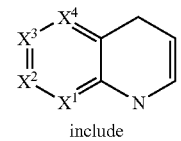

include

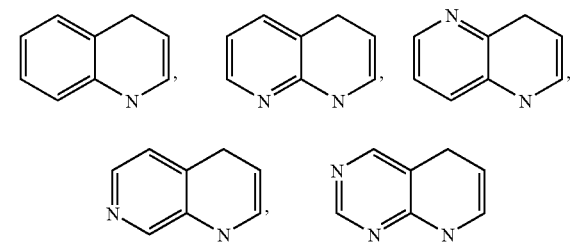

In the invention, a quinoline ring is particularly preferable.

In the invention, is preferable a compound represented by the foregoing general formula (I) wherein $X^1$ to $X^4$ are all C, and specifically an ester or amide derivative of 3-alkyl-4-oxo-1,4-dihydroquinoline-2-carboxylic acid represented by the following general formula (I') or a salt thereof.

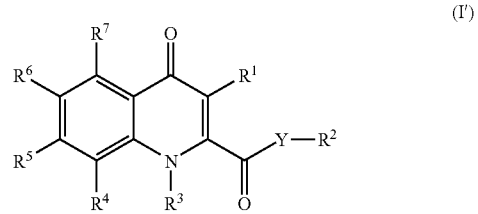

In the general formula, $X^1$ to $X^4$, Y, and $R^1$ to $R^7$ have the same meanings as defined above.

In the invention, is more preferable a compound represented by the foregoing general formula (I) wherein $X^1$ to $X^4$ are all C, and $R^3$ is H, and specifically an ester or amide derivative of 3-alkyl-4-oxo-1,4-dihydroquinoline-2-carboxylic acid represented by the following general formula (I") or a salt thereof.

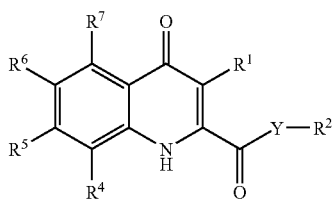

(I″)

In the general formula, $X^1$ to $X^4$, Y, and $R^4$ to $R^7$ have the same meanings as defined above.

In the invention, is further preferable a compound represented by the foregoing general formula (I″) wherein $R^2$ represents (a) a $C_1$ to $C_{10}$ alkyl group (provided that when X is O, $R^2$ represents a $C_5$ to $C_{10}$ alkyl group), or (b) a phenyl-$C_1$ to $C_6$ alkyl group (provided that any carbon-carbon bond of the $C_1$ to $C_{10}$ alkyl group may be inserted by —O—, —$NR^8$—, or —S(O)$_n$— (wherein $R^8$ represents H or a $C_1$ to $C_6$ alkyl, and n is 0, 1 or 2), and that the phenyl may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—); and more preferably, $R^2$ represents a $C_6$ to $C_8$ alkyl group or a benzyl group which may be substituted with one to three of halogen, $C_1$ to $C_6$ alkyl, $C_1$ to $C_6$ alkyl-O—, nitro, amino, $C_1$ to $C_6$ alkyl-N—, or di-$C_1$ to $C_6$ alkyl=N—.

Also, a compound wherein $R^1$ represents a methyl group is preferable. A compound wherein $R^4$ to $R^7$ are all H is preferable.

In the invention, the following compounds are particularly preferable.

N-Heptyl-3-methyl-4-oxo-1,4-dihydroquinoline-2-carboxamide

N-(4-Methylbenzyl)-3-methyl-4-oxo-1,4-dihydroquinoline-2-carboxamide

N-(3-Methoxybenzyl)-3-methyl-4-oxo-1,4-dihydroquinoline-2-carboxamide

Benzyl 3-methyl-4-oxo-1,4-dihydroquinoline-2-carboxylate

With respect to the compound of the invention, there are optical isomers (such as optically active compounds and diastereomers) depending on the kinds of the groups. Further, the compound of the invention includes a compound having an amide bond. There may be tautomers based on the amide bond. Especially, among the compounds of the invention, the ester or amide derivatives of 3-alkyl-4-oxo-1,4-dihydroquinoline-2-carboxylic acid represented by the general formula (I″) include the following tautomers.

The invention includes isolated isomers and mixed isomers thereof.

The compound (I) of the invention may form a salt with an acid or a base depending on the kinds of the substituents. Such a salt is a pharmaceutically acceptable salt. Specific examples include acid addition salts with an inorganic acid such as hydrochloric acid, hydrobromic acid, hydroiodic acid, sulfuric acid, nitric acid, and phosphoric acid, or with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid; salts with an inorganic base such as sodium, potassium, magnesium, calcium, and aluminum, or with an organic base such as methylamine, ethylamine, ethanolamine, lysine, and ornithine; and ammonium salts.

In addition, the invention includes various hydrates, solvates and crystal polymorphisms of the compound (I) of the invention and its salt. Moreover, the invention includes prodrugs of the substance of the formula (I) as obtained in the customary means. The prodrugs as used herein mean a compound having a substituent(s) capable of converting into the substituent(s) of the substance of the formula (I) by solvolysis or under physiological conditions, especially a compound that will be converted into the substance of the formula (I) within a living body. As the substituent to form the prodrug are enumerated those groups described in *Prog. Med.*, 5, 2157–2161 (1985) and *Iyakuhin No Kaihatsu* (Development of Drugs), Vol. 7, "Molecular Design", 163–198 (1990), by Hirokawa-shoten.

For example, there is enumerated a compound having a hydroxyl group substituted at the 1-position of the quinoline ring of the ester or amide derivative of 3-alkyl-4-oxo-1,4-dihydroquinoline-2-carboxylic acid (I″).

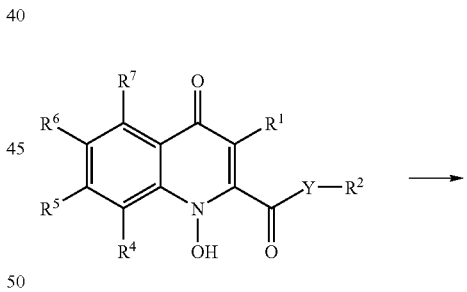

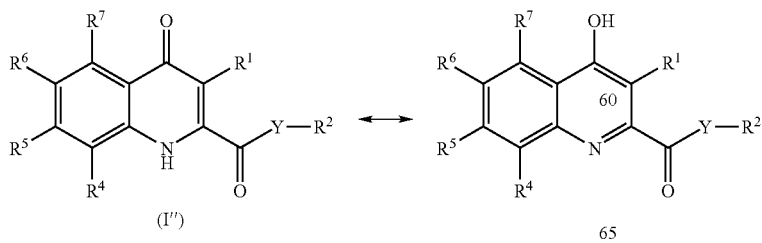

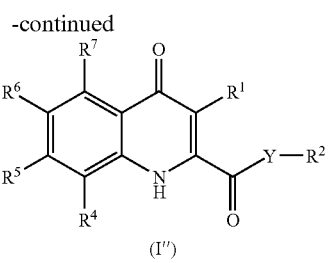

(Production Process)

The compound (I) and its salt of the invention can be produced through application of various known synthesis processes by utilizing the characteristic features based on the basic skeleton thereof or kinds of the substituents.

First Process:

Among the compounds of the invention, an amide derivative (Ia) having a substituted amino group as the substituent at the 2-position of the 1,4-dihydroquinoline ring is produced by reacting a carboxylic acid derivative represented by the general formula (II) with an amine represented by the general formula (III) to form an amide bond.

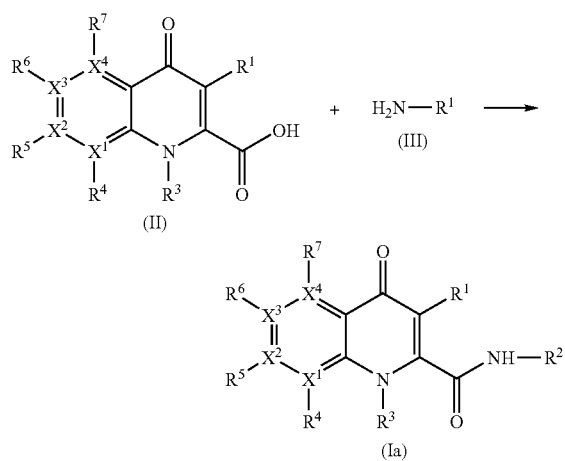

In the formulae, $X^1$ to $X^4$ and $R^1$ to $R^7$ have the same meanings as defined above.

The reaction is usually carried out in a usual solvent such as acetone, dioxane, tetrahydrofuran, diethyl ether, diisopropyl ether, acetonitrile, chloroform, dichloromethane, 1,2-dichloroethane, ethyl acetate, N,N-dimethylformamide (DMF), toluene, and pyridine, or a mixture thereof. The reaction may also be carried out in other arbitrary organic solvent so far as it does not adversely affect the reaction. Although the reaction temperature and reaction time are not particularly limited, the reaction is usually carried out at room temperature overnight. The reaction can be carried out in the presence of a catalyst such as 1-hydroxybenzotriazole (HOBt) and 4-dimethylaminopyridine (DMAP), and/or a condensing agent such as dicyclohexylcarbodiimide (DCC), 1-[3-(dimethylamino)propyl-3-ethylcarbodiimide hydrochloride (WSCD-HCl), and carbonyldiimidazole (CDI). Further, the reaction can also be carried out in the presence of N,N-dimethylformamide (DMF) via an acid chloride using thionyl chloride or oxalyl chloride. Alternatively, the reaction can be carried out via an active ester using an acid anhydride such as acetic anhydride, or an acid chloride such as mesyl chloride.

Second Process:

Among the compounds of the invention, an ester derivative (Ib) having an ester residue as the substituent at the 2-position of the 1,4-dihydroquinoline ring is produced by reacting the carboxylic acid derivative represented by the general formula (II) with an alcohol represented by the general formula (IV) to form an ester bond.

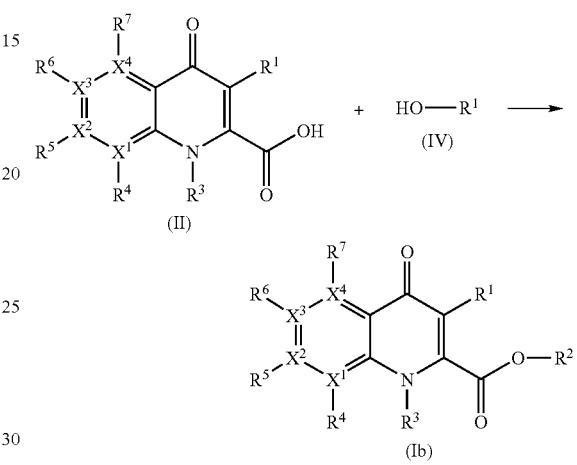

In the formulae, $X^1$ to $X^4$ and $R^1$ to $R^7$ have the same meanings as defined above.

The reaction is usually carried out in the foregoing usual solvent or a mixture thereof. The reaction may also be carried out in other arbitrary organic solvent so far as it does not adversely affect the reaction. Although the reaction temperature and reaction time are not particularly limited, the reaction is usually carried out at room temperature overnight. The reaction can be carried out in the presence of a catalyst such as 1-hydroxybenzotriazole (HOBt) and 4-dimethylaminopyridine (DMAP), and/or a condensing agent such as dicyclohexylcarbodiimide (DCC), 1-[3-(dimethyl-amino)propyl-3-ethylcarbodiimide hydrochloride (WSCD.HCl), and carbonyldiimidazole (CDI). Further, the reaction can also be carried out in the presence of N,N-dimethylformamide (DMF) via an acid chloride using thionyl chloride or oxalyl chloride. Alternatively, the reaction can be carried out via an active ester using an acid anhydride such as acetic anhydride, or an acid chloride such as mesyl chloride.

Incidentally, with respect to the compound of the invention, as described above, there may be the case where isomers such as a racemate, an optically active compound, and a diastereomer are present singly or as a mixture. The racemic compound can be introduced into a stereochemically pure isomer by using a proper starting material(s), or by general racemic resolution (such as a method in which the racemic compound is introduced into a diastereomer salt with a general optically active acid (such as tartaric acid), which is then subjected to optical resolution). Further, the mixture of diastereomers can be separated by a customary manner such as fractional crystallization and chromatography.

INDUSTRIAL APPLICABILITY

The invention exhibits a selective anti-bacterial action against *Helicobacter pylori* and is effective for the therapy of infections of *Helicobacter pylori* in human being and related bacteria belonging to the genus *Helicobacter* in animals. Further, the anti-*helicobacter pylori* agent of the invention is effective for prevention (including prevention of recurrence) or therapy of peptic ulcers (such as gastric or duodenal ulcer), inflammations (such as acute or chronic gastritis or duodenitis), diseases of upper digestive tracts such as gastric cancer, MALT (mucosa-associated lymphoid tissue) lymphoma, or chronic heart disease.

The actions of the compound of the invention were confirmed by the following pharmacological tests.

(1) In Vitro Anti-Bacterial Activity Test:

1) Preparation of Anti-Bacterial Substance-Containing Agar Plate:

A substance to be evaluated was dissolved in 100% DMSO, and the solution was subjected to two-fold series dilution. The diluted solution was charged in a sterilized round Petri dish, to which was then added 10 mL of a *brucella* agar medium (0.1% β-cyclodextrin or 5% sheep blood) which had been sterilized and kept at 50° C. After intimate mixing, the mixture was solidified. The ultimate concentration of DMSO is 1% or less.

2) Preparation of Inoculation Material and Result Judgment:

*Helicobacter pylori*, such as *Helicobacter* pylon ATCC43504, which had been cultured at 37° C. for 3 days in a multigas incubator ($N_2$: 80%, $CO_2$: 15%, $O_2$: 5%) using a *brucella* agar medium (containing 5% calf serum), was prepared using a *brucella* broth such that the number of bacteria was about $10^8$ per mL depending on the turbidity. The bacterial solution was similarly diluted with a *brucella* broth 100-fold, about 1 or 5 μL of which was then inoculated on the surface of a drug-containing agar medium using a micro-planter. The inoculated agar plate was cultured at 37° C. for 3 days (72 hours) in the foregoing multigas incubator. The cultured agar plate was observed, and a minimal drug concentration at which the proliferation was not observed was designated as MIC.

(2) In Vivo Anti-Bacterial Activity Test:

The infection test was carried out by using *Mongolian gerbils* as reported to be stably infected (*J. Gastroenterology* 31: supple IX, 24–28, 1996). An overnight cultured inoculum of ATCC43504 was inoculated into a stomach of overnight-fasted Mongolian gerbils (MGS/Sea, male, 4-week-old) About one week after the infection, the therapy was started by orally administering a drug to be evaluated dissolved in a solvent according to the customary manner in a dose of 10 mg/kg, 3 mg/kg or 1 mL/kg twice per day for three days. Next day after completion of the administration, the stomach was taken out and ground. A stomach homogenate solution was subjected to 10-fold series dilution, inoculated on a modified Skirrow medium, and then cultured at 37° C. for six to seven days under microaerophile conditions or 10% $CO_2$ conditions. The number of bacteria within the stomach was calculated from the number of grown bacteria.

Any of the compounds of Examples 1 to 4 of the invention exhibited a bacterial elimination effect from at a dose of 1 mg/kg. On the other hand, the following known compounds exhibited a bacterial elimination effect from at a does of 10 mg/kg.

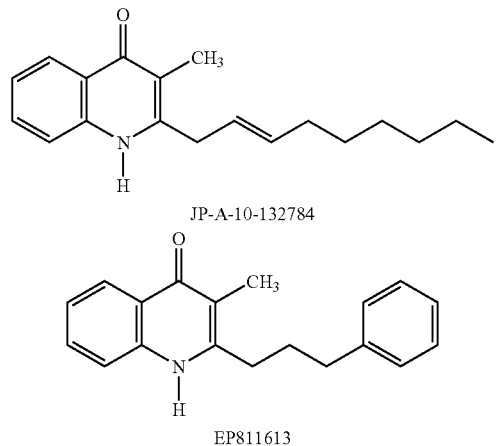

JP-A-10-132784

EP811613

Accordingly, it was confirmed that the compounds of the invention have a stronger bacterial elimination effect by oral administration to mammals as compared with the known anti-*helicobacter pylori* agents.

The drug containing the compound (I) of the invention or its salt and a pharmaceutically acceptable carrier can be prepared by a usually employed method using one or two or more of the compound represented by the general formula (I) or its salt and a pharmaceutical carrier, excipient and other additives as used for formulation. The administration may be in any form of oral administration by tablets, pills, capsules, granules, powders, liquids, etc., or parenteral administration by injections such as intravenous or intramuscular injection, suppositories, dermal administration, etc.

As a solid composition for the oral administration according to the invention, tablets, powders, or granules are used. In such a solid composition, one or more active substances are mixed with at least one inert diluent such as lactose, mannitol, glucose, hydroxypropyl cellulose, microcrystalline cellulose, starch, polyvinylpyrrolidone, magnesium metasilicate aluminate. The composition may contain additives other than the inert diluent, such as a lubricant such as magnesium stearate, a disintegrating agent such as cellulose calcium glycolate, a stabilizer such as lactose, and a dissolution aid such as glutamic acid and aspartic acid, according to the customary method. If desired, the tablets or pills may be coated by a sugar coating such as sugar, gelatin, hydroxypropyl cellulose, and hydroxypropylmethyl cellulose phthalate, or a film made of a gastric-soluble or intestinal soluble substance.

The liquid composition for oral administration contains a pharmaceutically acceptable emulsion agent, solution agent, suspending agent, syrup, or elixir and contains a generally employed inert diluent such as purified water and ethanol. In addition to the inert diluent, this composition may contain an auxiliary agent such as a wetting agent and a suspending agent, a sweetener, a flavor, an aromatic, or an antiseptic.

The injection for parenteral administration contains a sterile aqueous or non-aqueous solution agent, suspending agent or emulsion agent. Examples of the aqueous solution agent or suspending agent include distilled water or physiological saline for injection. Examples of the non-aqueous solution agent or suspending agent include propylene glycol, polyethylene glycol, vegetable oils such as olive oil, alcohols such as ethanol, and Polysolvate 80 (trade name). Such a composition may also contain an auxiliary agent such as an antiseptic, a wetting agent, an emulsifier, a dispersing agent, a stabilizer (such as lactose), and a dissolution aid (such as glutamic acid and aspartic acid). These compositions are sterilized by, for example, filtration through a bacteria-holding filter, compounding with an anti-bacterial agent, or irradiation. Further, these can be used by producing a sterile solid composition and dissolving it in sterile water or a sterile solvent for injection before the used.

Usually, in the case of the oral administration, it is proper that the dose of the drug per day is from about 0.001 to 30 mg per kg, and preferably from 0.1 to 5 mg per kg of the body weight and that the drug is administered once or dividedly two to four times. In the case of the intravenous administration, it is proper that the dose of the drug per day is from about 0.001 to 30 mg per kg of the body weight and that the drug is administered once or dividedly several times. The dose is properly determined depending on the individuals while taking into consideration the symptom, age and sex.

According to the invention, the compound (I) can be used singly or in combination with other anti-bacterial agents (preferably one to three kinds). Such other anti-bacterial agents can be used in combination simultaneously with the compound of the invention or after elapsing for a while.

Examples of such other anti-bacterial agents include nitroimidazole antibiotics (such as tinidazole and metronidazole), tetracycline series drugs (such as tetracycline, minocycline, and doxycycline), penicillin series drugs (such as amoxicillin, ampicillin, talampicillin, bacampicillin, lenampicillin, mezlocillin, and sultamicillin), cephalosporin series drugs (such as cefaclor, cefadroxil, cefalexin, cefpodoxime proxetil, cefixime, cefdinir, ceftibuten, cefatiam hexetil, cefetamet pivoxil, cefcapene pivoxil, sefiditoren pivoxil, and cefloxime axetil), penenm series drugs (such as faropenem and ritipenem acoxil), macrolide series drugs (such as erythromycin, oleandomycin, josamycin, midecamycin, rokitamycin, clarithromycin, roxithromycin, terithromycin, and azithromycin), lincomycin series drugs (such as lincomycin and clindamycin), aminoglycocide series drygs (such as paromomycin), quinolone series drugs (such as ofloxacin, lebofloxacin, norfloxacin, enoxacin, ciprofloxacin, lomefloxacin, tosufloxacin, fleroxacin, spafloxacin, temafloxacin, nadifloxacin, grepafloxacin, balfloxacin, prulifloxacin, gatifloxacin, sitafloxacin, and pazufloxacin), and nitrofurantoin. Further, combinations of the compound (I) of the invention with PPI (such as omeprazole, rabeprazole, and lansoprazole) or anti-ulcer agents (such as $H_2$ antagonists such as ranitidine, cimetidine, and famotidine, or gastric mucosal protective agents) fall within the scope of the invention.

BEST MODE FOR CARRYING OUT THE INVENTION

The invention will be described below in more detail with reference to the Referential Examples and Examples. As a matter of course, it should not be construed that the invention is limited thereto. In the nuclear magnetic resonance spectra (1H-NMR) described in physical properties, DMSO was used as a measurement solvent, and tetramethyl silane was used as an internal standard (δ: 0.00 ppm). The mass analysis (MS) was made by the fast atom bombardment (FAB).

REFERENTIAL EXAMPLE 1

Ethyl 3-methyl-4-oxo-1,4-dihydroquinoline-2-carboxylate (1) Aniline (51.1 g) and 21.4 g of Diethyl oxalpropionate were dissolved in 200 mL of benzene, to which was then added 4 mL of acetic acid, and the mixture was refluxed upon heating overnight by a Dean-Stark condenser. The solvent was distilled off to obtain a yellow oily substance.

(2) The compound obtained in (1) was dissolved in 200 mL of diphenyl ether, and the solution was heated at 250° C. for 30 minutes. After allowing to stand for cooling, the reaction mixture was poured into 600 mL of hexane, and precipitates were filtered out. The crystals were rinsed with diethyl ether and dried to obtain 36.7 g (63%) of the titled compound. MS: 232 ($M^+$+1).

REFERENTIAL EXAMPLE 2

3-Methyl-4-oxo-1,4-dihydroquinoline-2-carboxylic Acid

To 18.1 g of the compound obtained in Referential Example 1 was added 170 mL of a 1N sodium hydroxide aqueous solution, and the mixture was refluxed upon heating for 30 minutes. After allowing to stand for cooling, hydrochloric acid (concentrated hydrochloric acid:water=1:1) was gradually added, and precipitates were collected by filtration and rinsed with dilute hydrochloric acid, followed by drying. To the resulting crystals was added 100 mL of acetonitrile, and the mixture was refluxed upon heating for 30 minutes. After allowing to stand for cooling, crystals were collected by filtration and dried to obtain 15.6 g (98%) of the titled compound. MS: 202 ($M^+$−1).

EXAMPLE 1

N-Heptyl-3-methyl-4-oxo-1,4-dihydroquinoline-2-carboxamide

The compound (3.252 g) obtained in Referential Example 2, 2.39 g of HOBt, and 3.385 g of WSCD were dissolved in 40 mL of DMF. After dropwise addition of 2.041 g of heptylamine, the reaction mixture was stirred overnight. Saturated sodium chloride aqueous solution and ethyl acetate were added, and the mixture was stirred for one hour. Precipitates were collected by filtration, rinsed with dilute hydrochloric acid, ethyl acetate, and water, and then dried to obtain 4.437 g (92%) of the titled compound.

1H-NMR: 0.87 (t, 2H), 1.28 to 1.34 (m, 8H), 1.51 to 1.58 (m, 2H), 1.98 (s, 3H), 3.27 (q, 2H), 7.27 to 7.31 (m, 1H), 7.58 to 7.65 (m, 2H), 8.08 to 8.10 (m, 1H), 8.81 (t, 1H), 11.84 (s, 1H). MS (m/z): 301 ($M^+$+1).

Compounds of the Examples 2 to 5 were obtained in the same manner as in Example 1.

EXAMPLE 2

N-(4-Methylbenzyl)-3-methyl-4-oxo-1,4-dihydroquinoline-2-carboxamide

1H-NMR: 1.96 (s, 3H), 2.30 (s, 3H), 4.46 (d, 2H), 7.18 (d, 2H), 7.27 to 7.31 (m, 3H), 7.60 to 7.65 (m, 2H), 8.09 (d, 1H), 9.32 (s, 1H), 11.89 (s, 1H). MS (m/z): 307 ($M^+$+1).

EXAMPLE 3

N-(3-Methoxybenzyl)-3-methyl-4-oxo-1,4-dihydro-quinoline-2-carboxamide

1H-NMR: 1.99 (s, 3H), 3.76 (s, 3H), 4.50 (d, 2H), 6.85 to 6.87 (m, 1H), 6.96 to 6.97 (m, 2H), 7.27 to 7.32 (m, 2H), 7.60 to 7.65 (m, 2H), 8.09 (d, 1H), 9.35 (t, 1H), 11.91 (s, 1H). MS (m/z): 323 ($M^++1$).

EXAMPLE 4

N-{2-[Ethyl-(3-methylphenyl)amino]ethyl}-3-methyl-4-oxo-1,4-dihydroquinoline-2-carboxamide 1H-NMR: 1.10 (t, 3H), 1.99 (s, 3H), 2.24 (s, 3H), 3.39 (q, 2H), 3.45 (s, 4H), 6.42 (d, 1H), 6.59 to 6.62 (m, 2H), 7.05 (t, 1H), 7.28 to 7.32 (m, 1H), 7.60 to 7.66 (m, 2H), 8.09 (d, 2H), 8.95 (s, 1H), 11.86 (s, 1H). MS (m/z): 364 ($M^++1$).

EXAMPLE 5

N-(4-Phenylbutyl)-3-methyl-4-oxo-1,4-dihydro-quinoline-2-carboxamide

1H-NMR: 1.53 to 1.70 (m, 4H), 1.96 (s, 3H), 2.63 (t, 2H), 3.29 to 3.34 (m, 2H), 7.16 to 7.30 (m, 6H), 7.57 to 7.64 (m, 2H), 8.09 (d, 1H), 8.83 (t, 1H), 11.83 (s, 1H). MS (m/z): 335 ($M^++1$).

EXAMPLE 6

Benzyl 3-methyl-4-oxo-1,4-dihydroquinoline-2-carboxylate

The compound (5.615 g) obtained in Referential Example 2, 4.209 g of HOBt, 5.879 g of WSCD, and 138 mg of DMAP were dissolved in a mixed solvent of 55 mL of methylene chloride and 20 mL of DMF. After dropwise addition of 3.341 g of benzyl alcohol, the reaction mixture was stirred overnight, to which was then added saturated sodium chloride aqueous solution. Precipitates were collected by filtration, rinsed with ethyl acetate and water, and then dried to obtain 5.109 g (63%) of the titled compound.

1H-NMR: 2.19 (s, 3H), 5.49 (s, 3H), 7.31 to 7.35 (m, 1H), 7.37 to 7.46 (m, 3H), 7.53 to 7.55 (m, 2H), 7.65 to 7.69 (m, 1H), 7.81 (d, 1H), 8.08 to 8.10 (m, 1H), 11.78 (s, 1H). MS (m/z): 294 ($M^++1$).

Further, the compounds represented by the chemical structural formulae in the table can be easily produced in substantially same manners as in the Examples or production processes, or by undergoing slight modifications within the range obvious to those skilled in the art. Incidentally, symbols shown in the table have the following meanings. No.: compound number, Me: methyl, Cl: chloro, F: fluoro

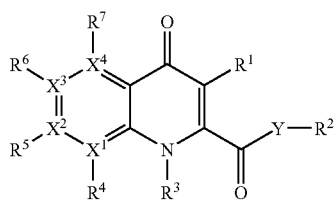

(I)

| No. | $X^1$ | $X^2$ | $X^3$ | $X^4$ | Y | $R^1$ | $R^2$ | $R^3$ | $R^4$ | $R^5$ | $R^6$ | $R^7$ |
|---|---|---|---|---|---|---|---|---|---|---|---|---|
| 1 | C | C | C | C | NH | Me | (E)-2-(methylsulfonyl)vinyl-phenyl | H | H | H | H | H |
| 2 | C | C | C | C | NH | Me | N-propyl-benzamide | H | H | H | H | H |
| 3 | C | C | C | C | NH | Me | propyl-N(Me)-benzyl | H | H | H | H | H |
| 4 | C | C | C | C | NH | Me | propyl-O-benzyl | H | H | H | H | H |

-continued

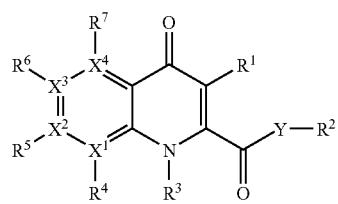
(I)

| No. | X¹ | X² | X³ | X⁴ | Y | R¹ | R² | R³ | R⁴ | R⁵ | R⁶ | R⁷ |
|---|---|---|---|---|---|---|---|---|---|---|---|---|
| 5 | C | C | C | C | NH | Me | 4-(NMe₂)-phenyl-ethyl | H | H | H | H | H |
| 6 | C | C | C | C | NH | Me | 4-(CO₂H)-phenyl-ethyl | H | H | H | H | H |
| 7 | C | C | C | C | NH | Me | 2-ethyl-3-methyl-4-[2-(pyridin-4-ylmethylthio)ethoxy]pyridine | H | H | H | H | H |
| 8 | N | C | C | C | NH | Me | 5-phenylpentyl | H | — | H | H | H |
| 9 | N | C | N | C | NH | Me | 5-phenylpentyl | H | — | H | — | H |
| 10 | C | C | C | C | NH | Me | 5-phenylpentyl | Me | H | H | H | H |
| 11 | C | C | C | C | NH | Me | 5-phenylpentyl | 1-methyl-2-fluorocyclopropyl | H | H | H | H |
| 12 | C | C | C | C | NH | Me | 5-phenylpentyl | benzyl | H | H | H | H |
| 13 | C | C | C | C | NH | Me | 5-phenylpentyl | 2-methyl-3-methoxypropyl | 1,4-dimethylpiperazinyl | | F | H |

-continued

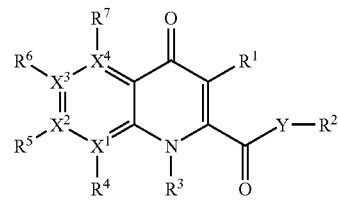

(I)

| No. | X¹ | X² | X³ | X⁴ | Y | R¹ | R² | R³ | R⁴ | R⁵ | R⁶ | R⁷ |
|---|---|---|---|---|---|---|---|---|---|---|---|---|
| 14 | C | C | C | C | O | Me | benzyl-CH₂ | Me | H | H | H | H |
| 15 | C | C | C | C | O | Me | benzyl-CH₂ | fluorocyclopropylmethyl | H | H | H | H |
| 16 | C | C | C | C | O | Me | benzyl-CH₂ | H | benzyl | H | H | H |
| 17 | N | C | C | C | O | Me | benzyl-CH₂ | H | — | H | H | H |
| 18 | C | C | C | N | O | Me | benzyl-CH₂ | H | H | H | — | H |
| 19 | C | N | C | C | O | Me | benzyl-CH₂ | H | H | — | H | H |
| 20 | C | C | C | C | O | Me | benzyl-CH₂ | Me₂CHCH₂O— | Me-N(piperazine)N- | F | H | |

The invention claimed is:

1. An ester compound of formula (I) or a pharmaceutically acceptable salt thereof, wherein formula (I) is:

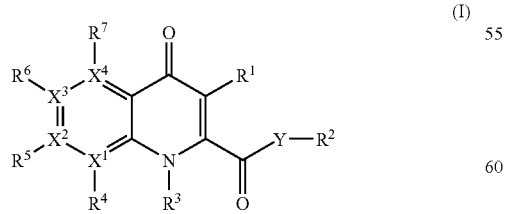

(I)

wherein:
X¹ to X⁴ each independently represents C or N, provided that at least three of X¹ to X⁴ represents C;
Y represents O;
R¹ represents a $C_1$ to $C_6$ alkyl group;
R² represents (a) a $C_3$ to $C_{10}$ alkyl group, or (b) an aryl-$C_1$ to $C_{10}$ alkyl group and that the aryl may be substituted with from one to three of halogen, $C_1$ to $C_6$ alkyl, $C_1$ to $C_6$ alkyl-O—, nitro, cyano, amino, hydroxycarbonyl, $C_1$ to $C_6$ alkyl-NH—, or di-$C_1$ to $C_6$ alkyl=N—;
R³ represents H, a $C_1$ to $C_6$ alkyl group, an aryl-$C_1$ to $C_6$ alkyl group, a heteroaryl-$C_1$ to $C_6$ alkyl group, a cycloalkyl-$C_1$ to $C_6$ alkyl group, an aryl group, a heteroaryl group, or a cycloalkyl group, provided that the aryl, heteroaryl, and cycloalkyl group may each be substituted with from one to three of halogen, $C_1$ to $C_6$ alkyl, $C_1$ to $C_6$ alkyl-O—, nitro, cyano, amino, hydroxycarbonyl, $C_1$ to $C_6$ alkyl-NH—, or di-$C_1$ to $C_6$ alkyl=N—; and
R⁴ to R⁷ may be the same or different and each represents H, a halogen, a nitro group, a cyano group, an amino group, a hydroxycarbonyl group, a $C_1$ to $C_6$ alkyl group, a $C_1$ to $C_6$ alkyl-O— group, a $C_1$ to $C_6$ alkyl-NH group, or a di-$C_1$ to $C_6$ alkyl=N— group, provided that in the case where $X^1$ to $X^4$ each represents N, $R^4$ to $R^7$ to be bound thereto are not present and that $R^3$ and $R^4$ may be taken together to form a linear or branched $C_1$ to $C_8$ alkylene which may be inserted by N, O or S.

2. The ester compound or its pharmaceutically acceptable salt according to claim 1, wherein $X^1$ to $X^4$ are all C.

3. The ester compound or its pharmaceutically acceptable salt according to claim 1, wherein $R^3$ is H.

4. The ester compound or its pharmaceutically acceptable salt according to claim 1, wherein $R^2$ represents (a) $C_5$ to $C_{10}$ alkyl group, or (b) a phenyl-$C_1$ to $C_6$ alkyl group, provided that the phenyl may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

5. The ester compound or its pharmaceutically acceptable salt according to claim 4, wherein $R^2$ represents (a) a $C_6$ to $C_8$ alkyl group or (b) a benzyl group which may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

6. The ester compound or its pharmaceutically acceptable salt according to claim 1, wherein $R^1$ represents a methyl group.

7. The ester compound or its pharmaceutically acceptable salt according to claim 1, wherein $R^4$ to $R^7$ are all H.

8. The ester compound or its pharmaceutically acceptable salt according to claim 1, which is Benzyl 3-methyl-4-oxo-1,4-dihydroquinoline-2-carboxylate, or a salt thereof.

9. A pharmaceutical composition comprising an ester compound according to claim 1 or its pharmaceutically acceptable salt and a pharmaceutically acceptable carrier.

10. The ester compound or its pharmaceutically acceptable salt according to claim 2, wherein $R^3$ is H.

11. The ester compound or its pharmaceutically acceptable salt according to claim 10, wherein $R^2$ represents (a) a $C_5$ to $C_{10}$ alkyl group, or (b) a phenyl-$C_1$ to $C_6$ alkyl group, provided that the phenyl may be substituted with from one to three of halogen, $C_1$ to $C_6$ alkyl, $C_1$ to $C_6$ alkyl-O—, nitro, amino, $C_1$ to $C_6$alkyl-NH—, or di-$C_1$ to $C_6$alkyl=N—.

12. The ester compound or its pharmaceutically acceptable salt according to claim 11, wherein $R^2$ represents (a) a $C_6$ to $C_8$ alkyl group or (b) a benzyl group which may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

13. The ester compound or its pharmaceutically acceptable salt according to claim 11, wherein $R^1$ represents a methyl group.

14. The ester compound or its pharmaceutically acceptable salt according to claim 13, wherein $R^4$ to $R^7$ are all H.

15. The ester compound or its pharmaceutically acceptable salt according to claim 2, wherein $R^2$ represents (a) a $C_5$ to $C_{10}$ alkyl group, or (b) a phenyl-$C_1$ to $C_6$ alkyl group, provided that the phenyl may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

16. The ester compound or its pharmaceutically acceptable salt according to claim 15, wherein $R^2$ represents (a) a $C_6$ to $C_8$ alkyl group or (b) a benzyl group which may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

17. The ester compound or its pharmaceutically acceptable salt according to claim 2, wherein $R^1$ represents a methyl group.

18. The ester compound or its pharmaceutically acceptable salt according to claim 2, wherein $R^4$ to $R^7$ are all H.

19. The ester compound or its pharmaceutically acceptable salt according to claim 3, wherein $R^2$ represents (a) a $C_5$ to $C_{10}$ alkyl group, or (b) a phenyl-$C_1$ to $C_6$ alkyl group, provided that the phenyl may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

20. The ester compound or its pharmaceutically acceptable salt according to claim 19, wherein $R^2$ represents (a) a $C_6$ to $C_8$ alkyl group or (b) a benzyl group which may be substituted with from one to three of halogen, $C_1$ to $C_6$ alkyl, $C_1$ to $C_6$ alkyl-O—, nitro, amino, $C_1$ to $C_6$ alkyl-NH—, or di-$C_1$ to $C_6$ alkyl=N—.

21. The ester compound or its pharmaceutically acceptable salt according to claim 3, wherein $R^1$ represents a methyl group.

22. The ester compound or its pharmaceutically acceptable salt according to claim 3, wherein $R^4$ to $R^7$ are all H.

23. The ester compound or its pharmaceutically acceptable salt according to claim 4, wherein $R^1$ represents a methyl group.

24. The ester compound or its pharmaceutically acceptable salt according to claim 4, wherein $R^4$ to $R^7$ are all H.

25. The ester compound or its pharmaceutically acceptable salt according to claim 5, wherein $R^1$ represents a methyl group.

26. The ester compound or its pharmaceutically acceptable salt according to claim 5, wherein $R^4$ to $R^7$ are all H.

27. The ester compound or its pharmaceutically acceptable salt according to claim 6, wherein $R^4$ to $R^7$ are all H.

* * * * *

UNITED STATES PATENT AND TRADEMARK OFFICE
CERTIFICATE OF CORRECTION

PATENT NO. : 7,183,412 B2
APPLICATION NO. : 10/992134
DATED : February 27, 2007
INVENTOR(S) : Kazami et al.

It is certified that error appears in the above-identified patent and that said Letters Patent is hereby corrected as shown below:

On the title page, item (57), lines 3-4, "4-oxo-1,4-dihydroqunoline-2-carboxylic" should read --4-oxo-1,4-dihydroquinoline-2-carboxylic--.

Column 18, line 52, "group and" should read --group, and--.

Column 19, line 42, "$C_6$alkyl-NH-, or di-$C_1$ to $C_6$alkyl=N-." should read --$C_6$ alkyl-NH-, or di-$C_1$ to $C_6$ alkyl=N-.--.

Signed and Sealed this

Fifteenth Day of May, 2007

JON W. DUDAS
*Director of the United States Patent and Trademark Office*